(12) United States Patent
Carpenter et al.

(10) Patent No.: US 6,413,778 B1
(45) Date of Patent: Jul. 2, 2002

(54) METHODS FOR THE DETECTION AND IDENTIFICATION OF CRYSTALS IN BIOLOGICAL FLUIDS

(75) Inventors: Charles R. Carpenter, Scarborough; Melanie Tornberg, South Berwick; Genevieve Clark, Standish, all of ME (US)

(73) Assignee: Idexx Laboratories, Westbrook, ME (US)

( * ) Notice: Subject to any disclaimer, the term of this patent is extended or adjusted under 35 U.S.C. 154(b) by 0 days.

(21) Appl. No.: 09/235,124

(22) Filed: Jan. 21, 1999

(51) Int. Cl.$^7$ ............................................. G01N 33/48
(52) U.S. Cl. ...................... 436/4; 436/164; 436/177; 435/4; 435/28; 422/55; 422/56; 422/61
(58) Field of Search ................... 436/164, 169, 436/4, 177, 166; 435/28, 4; 422/55, 56, 61

(56) References Cited

U.S. PATENT DOCUMENTS

| | | | |
|---|---|---|---|
| 3,731,806 A | | 5/1973 | McCormick .................. 210/94 |
| 3,768,978 A | | 10/1973 | Grubb, et al. |
| 4,225,669 A | * | 9/1980 | Melnick et al. ............... 435/29 |
| 4,235,601 A | * | 11/1980 | Deutsch et al. ................ 435/4 |
| 4,455,371 A | * | 6/1984 | Richardson et al. .......... 435/25 |
| 4,683,209 A | * | 7/1987 | Ismail et al. .................. 436/14 |
| 4,727,019 A | | 2/1988 | Valkirs et al. ................... 435/5 |
| 4,912,035 A | * | 3/1990 | Belly et al. .................... 435/29 |
| 4,992,365 A | * | 2/1991 | Hyman ......................... 435/34 |
| 5,264,348 A | * | 11/1993 | Schick et al. ................... 435/4 |
| 5,352,410 A | | 10/1994 | Hansen, et al. ............... 422/58 |
| 5,824,495 A | * | 10/1998 | Hemstreet, III et al. ... 435/40.5 |
| 5,891,733 A | * | 4/1999 | Inoue ........................... 436/63 |

FOREIGN PATENT DOCUMENTS

| | | | |
|---|---|---|---|
| EP | 0 307 566 A | | 3/1989 |
| EP | 0 780 678 A | | 6/1997 |
| EP | 0 841 403 A | | 5/1998 |

OTHER PUBLICATIONS

Chelfouh, N. et al., "Characterization of Urinary Calculi: In Vitro Study of Twinkling Artifact" Revealed by Color–Flow Sonography, AJR. American Journal of Roentgenology, (Oct. 1998) 171 (4) 1055–60, XP–000901742, the whole document.
Tisellus, H., "Crystalluria in Patients With Calcium Stone Disease," *The Journal of Urology*, 161(5) (1999).

* cited by examiner

*Primary Examiner*—John Kim
(74) *Attorney, Agent, or Firm*—McDonnell Boehnen Hulbert & Berghoff

(57) ABSTRACT

The present invention relates to devices, methods and kits for the detection and identification of crystals which may be present in a biological fluid, such as urine from a cat. The device may include a filter and an absorbent material. The fluid may be transferred onto the filter, and fluid passes through the filter and into the absorbent material, thereby isolating crystals on a surface of or within the structure of the filter or membrane. The crystals are then available for staining which will reveal a determining component of the crystals. The device may also include a member for inhibiting backflow from the absorbent material to the filter.

The present invention also provides methods for detecting and identifying crystals which may be present in biological fluids. The methods include the steps of isolating the crystals on the surface of or within the structure of a filter or membrane, and contacting the crystals with an indicator which is specific for a determining component of the crystals type.

Also provided are kits which include the devices of the present invention, and reagents and other materials necessary to conduct the methods of the present invention.

23 Claims, 1 Drawing Sheet

METHODS FOR THE DETECTION AND IDENTIFICATION OF CRYSTALS IN BIOLOGICAL FLUIDS

This invention relates in general to devices for separating crystals from urine or other biological fluids and ascertaining their chemical identity. Also provided are methods for detecting and identifying crystals which may be present in urine or other biological fluids, and kits containing the devices and other materials and reagents needed to conduct the methods.

BACKGROUND OF THE INVENTION

Crystalluria, the presence of crystals in the urine, is a common problem which afflicts household pets such as cats and dogs. The formation of crystals and mucus in the urinary tract is a potentially life threatening condition in these animals. It is indicative of the predilection to form uroliths or stones, and can ultimately lead to a complete obstruction of the urinary system. Some studies have recorded that almost 10% of male cats and over 3% of female cats are affected by this disease.

Urine crystals may be of several different types. Most commonly crystals are formed of struvite (magnesium-ammonium-phosphate), oxalate, urate, cystine, or silicate, but may also be composed of other materials such as bilirubin, calcium carbonate, or calcium phosphate. Struvites and calcium oxalates combined comprise over 88% of the uroliths found in cats and dogs and therefore represent the cause of the great majority of these animal medical problems. The occurrence of crystalluria within these animal populations varies according to species, breed, diet, sex, age, and genetic pre-disposition. Crystalluria also occurs in a variety of other mammals. For example, it is known that calcium carbonate crystals can form in horses, rabbits, guinea pigs, and goats.

Present methods of detecting and identifying urine crystals rely on a high level of skill of a person who examines the crystals under a microscope and makes distinctions between the different types of crystals that may be present. It is sometimes required for the sample to be sent to a commercial laboratory for the analysis.

The term "habit" is commonly used by minerologists to refer to the characteristic shape or shapes of mineral crystals. Different crystal types exhibit different habits which a skilled person is able to differentiate. The judgment is based largely on the apparent structure or habit of the crystals. These methods involve specific skills, significant handling of the specimen, and are both time consuming and expensive. Microscopic detection and identification of the crystals is further complicated by the fact that their appearance can be influenced by the variable conditions of their formation, growth, and dissolution. The sensitivity of this method is also limited as it is not uncommon for the technician to fail to detect small numbers of crystals which may be present. This method of identifying the crystals also involves significant handling of the sample since it typically requires a volume of 5–10 mls of urine, which then must be concentrated to enhance the population of crystals within the examined specimen. Concentration is normally accomplished by centrifugation at 2500 rpm for 5–10 minutes, aspiration of all but 0.5 to 1.0 ml of fluid, and resuspension of the pellet.

The microscopist bases the judgment of crystal type on the physical characteristics or habit of the crystals present. Calcium oxalate dihydrate crystals typically are colorless and have a characteristic octahedral or envelope shape, having the appearance under a light microscope of squares whose corners are connected by intersecting diagonal lines. Struvite crystals are known for their colorless, orthorhombic, "coffinlid" shape, although frequently other, irregular forms are seen. They often have three to six or more sides and often have oblique ends. Cystine crystals exhibit a colorless hexagonal shape with equal or unequal sides. They may appear singly but usually aggregate in layers. As is evident from these descriptions, the differentiation of these different crystal types is based largely on subjective criteria, and is therefore prone to human error. For example, skilled persons sometimes have difficulty distinguishing struvite crystals from cystine. Calcium carbonate crystals may form as large yellow-brown or colorless spheroids with radial striations, or smaller crystals with round, ovoid, or dumbbell shapes.

Furthermore, the outer appearance of a crystal may not always correlate with its true chemical identity. For example, kidney stones are usually comprised of calcium oxalate, struvite, or cystine. However, crystals sometimes are comprised of a calcium oxalate core covered by an outer layer of struvite. Similarly, they may be comprised of a struvite core covered by an outer layer of calcium oxalate. Therefore, such crystals can be very deceiving even to the skilled person who is trying to ascertain their identity based largely on the external appearance of the crystals. The distinction is important, since the treatment programs for struvite and calcium oxalate crystals are very different.

Furthermore, before existing chemical and enzymatic analyses can be performed on crystals from urine or other biological fluids, it is necessary to first remove certain materials which are normally present and which interfere with these reactions, such as free magnesium, oxalate, and other substances. These materials are removed because they are not indicative of the presence of crystals when they are in the dissolved state. Therefore the use of these methods involves the further inconvenience of having to remove small molecular weight interfering substances such as oxalates which are typically removed by activated charcoal prior to testing.

Because of the time and expense involved in making accurate determinations of the presence and type of crystals, many veterinarians simply measure the pH of a urine sample, and make prescriptive decisions based on this criteria alone. This often results in needless changes to the animal's diet, and unnecessary inconvenience to the owner and stress on the animal.

The present invention provides a device for the convenient, rapid, and accurate determination of crystals which may be present in urine or other biological fluids and their identity. The device is inexpensive, disposable, specific, and requires only very small sample volumes. It also eliminates the need and consequent delay and expense of transmitting samples to a commercial laboratory for analysis. This results in quicker treatment for the affected animal and avoids additional stress on the animal caused by unnecessary dietary changes and inconvenience to the animal owner. Another important advantage is that the analysis of the urine crystals is based on more objective criteria, sharply reducing human error as a source of inaccuracy. Using the present invention, one is able to determine the presence of urinary crystals and identify the crystal type with almost 100% sensitivity and accuracy.

The present invention also discloses methods for detecting and identifying crystals which may be present in biological fluids, including urine. The methods may be conveniently performed in the veterinarian's office during the time typically taken for an office visit. Unlike currently available methods, a high level of training and skill is not necessary to successfully and confidently identify the crystal types, and the method can be learned in a matter of minutes.

The present invention also discloses kits which may include the devices of the present invention and reagents necessary for conducting the methods of the present invention. The kits enable the veterinarian or other animal caretaker to have conveniently available everything needed to conduct the assay and detect and identify any crystals which may be present. The kits have a shelf life of at least six months and may last one year or more, and may be conveniently stored in a small space until needed. The kits may include reagents necessary to conduct the assay in a ready-to-use format, thereby eliminating the need for mixing or preparing reagents.

SUMMARY OF THE INVENTION

The present invention relates to devices, methods, and kits for the rapid detection and identification of crystals which are suspected of being present in urine or other biological fluids. The devices of the present invention contain a filter, and may also contain an absorbent material. Crystals which are suspected of being present in urine or other biological fluids are isolated on or within the filter. The crystals may be isolated on the surface of or within the structure of the filter. The absorbent material serves to facilitate the drawing of liquid through the filter and into its absorbent material, thus isolating the crystal on or within the structure of the filter. Once isolated, the crystals will be available for staining with an indicator reagent specific for a determining component of the crystal.

In a preferred embodiment, the device may further contain a member which inhibits flow from the absorbent material to the filter and which may be placed between the absorbent material and the filter. The filter, absorbent material, and member for inhibiting flow from the absorbent material to the filter may be in positional relationship such that fluid passes through the filter, through the member for inhibiting flow from the absorbent material to the filter, and into the absorbent material. The member for inhibiting flow from the filter to the absorbing material may be made of polyethylene. In a preferred embodiment, the member may be a disk of porous polyethylene.

In preferred embodiments, the filter may be a filter with a graded pore structure. In various embodiments, the filter may be selected from, but is not limited to, an A/E glass filter, glass fiber, mylar, WHATMAN D28® filter, WHATMAN GD-1® filter, nitrocellulose, HEMASEP V®, HEMASEP L® filter, or SUPOR® polyethersulfone filter. The biological fluid may be urine, blood, blood products, or interstitial fluid.

In another aspect, the present invention provides methods of detecting and isolating crystals which may be present in urine or other biological fluids. The methods of the present invention may consist of the steps of isolating the crystals on or within a filter, contacting the crystals with an indicator reagent which is specific for a determining component of the crystals, and determining the presence and identity of the crystals.

The methods may further consist of a step of washing the crystals to wash away contaminants which may interfere with the indicator reaction. This wash step may be necessary in some chemistries to obtain an optimal indicator reaction. This washing step may further accomplish a disintegration action on the crystals thereby exposing a determining component of the crystals. There may be an additional washing step performed after the step of contacting the crystals with the indicator. This step may be combined with the initial wash step by using a wash that both washes and acts to partially disintegrate the crystal. The determining component thus exposed may react with dye or substrate for that specific determining component of the crystal. In preferred embodiments, the presence of the determining component will cause a visible color change on the surface of or within the filter or membrane. The additional wash step may clarify the color change for easier interpretation.

In preferred embodiments, the crystals which are suspected of being present may be oxalate crystals, or struvite crystals. The indicating system may be oxalate oxidase, a peroxidase and an indicator. In preferred embodiments, the peroxidase may be horseradish peroxidase. The indicator may also be a precipitating magnesium binding dye, such as magneson dye, or a calcium binding dye. In preferred embodiments, the indicator may be these or other precipitating dyes which form insoluble complexes with various analytes.

The present invention also provides kits for detecting and identifying crystals which are suspected of being present in urine or another biological fluid. The kits may include a device of the present invention for detecting and identifying crystals which are suspected of being present in a biological fluid and at least one reagent for detecting and identifying the crystals. The reagent(s) provided in the kit may be an indicator reagent or system useful for practicing the methods of the present invention. The kit may also include other reagents useful for practicing the methods of the present invention.

DETAILED DESCRIPTION OF THE INVENTION

Figure 1:
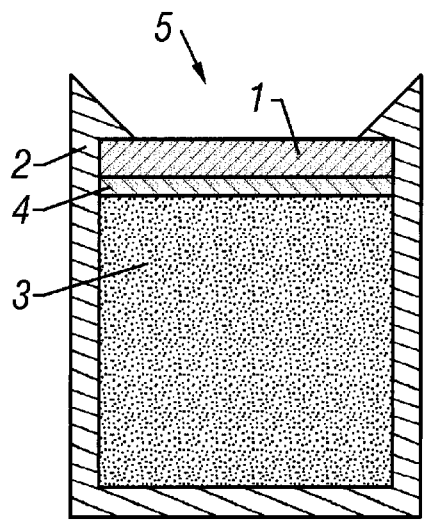
FIG. 1 is a schematic of one embodiment of the present invention for detecting and identifying crystals which may be present in a biological fluid. The Figure is an exposed side view showing the interior portion of the device.

A device of the invention is generally illustrated in FIG. 1. Referring to FIG. 1, the device of the present invention comprises a filter which is capable of retaining crystals which may be present in a biological fluid on its surface or within its structure. The device may also comprise an absorbent material 3 which serves to draw fluid through the filter 1. The filter may have pore sizes which are small enough to retain the crystals on its surface or within its structure.

In a preferred embodiment, the filter will have a graded pore structure with pore diameters which generally decrease as fluid travels further into the filter. This type of pore structure enables the introduction of the crystals into the filter and their retention in its structure as the pore sizes generally decrease further into the structure of the filter, and also permits the crystals to be held in place and washed while still being retained in the filter. By filter is meant anything that will function to separate components of a mixture by filtration, such as filters or membranes. By "optimal filter" is meant a HEMASEP V®, HEMASEP L®, SUPOR® polyethersulfone, WHATMAN D28®, WHATMAN GD-1®, nitrocellulose, or mylar filter. By "preferred filter" is meant a HEMASEP V®, HEMASEP L®, SUPOR® polyethersulfone, WHATMAN D28®, or WHATMAN GD-1® filter.

It is also preferred that the filter be capable of resisting staining or of being destained without appreciably removing stain from the crystals, so that stained crystals will be more easily visible in or on the filter. In a particularly preferred embodiment, when the crystal is struvite the filter will be a HEMASEP V® membrane or its equivalent. In another particularly preferred embodiment, when the crystal is oxalate, the filter will be a HEMASEP L® membrane or its equivalent. The person of ordinary skill in the art will realize that other filters may be used in the present invention including, but not limited to, A/E glass fiber, GF/DVA glass fiber, mylar, WHATMAN D28®, WHATMAN GD-1®, nitrocellulose, SUPOR® polyethersulfone, or any of their equivalents.

The person of ordinary skill will realize that any material or filter which is able to retain crystals on its surface or within its structure while allowing liquid to pass through, and which is capable of resisting staining or of being destained, will be suitable for use in the devices and kits of the present invention. Therefore, the embodiments of the filter described above are provided as examples, and are not intended to be limiting.

The filter may be retained within a housing or holding member 2. The housing 2 may be made of glass, plastic, or other suitable material. In a preferred embodiment, the housing 2 may comprise an ICON® filter device or its equivalent. Absorbent material 3 may be packed into the housing member 2 with one of the filters described above, or its equivalent. However, in other embodiments, the housing member 2 may comprise any type of filter or device which is capable of holding the filter 1 in place while the biological fluid is applied to and allowed to pass through it. In one embodiment, the filter 1 may be held in direct contact with the absorbent material 3.

The present invention may also comprise an absorbent material 3 adjoining the filter 1 which is able to draw fluid through the filter 1 and absorb the fluid. The absorbent material 3 may be an absorbent block. The selection of the absorbent material is not critical and a variety of fibrous materials may be used. In a preferred embodiment, the absorbent material 3 may be a cellulose-based absorbent material. For example, the material may be cellulose acetate with the fibers oriented as in a cigarette filter. Alternatively the absorbent material may be a cellulose block. However, the person of ordinary skill will realize that the material may be any material capable of drawing fluid through the filter 1 and absorbing the fluid including, but not limited to, polyester or polyolefin. The person of ordinary skill in the art will also readily realize that other methods of drawing fluid through the filter may be used, such as by suction, gravity, the application of external pressure, or any method capable of drawing or forcing fluid through the filter 1.

Figure 2:
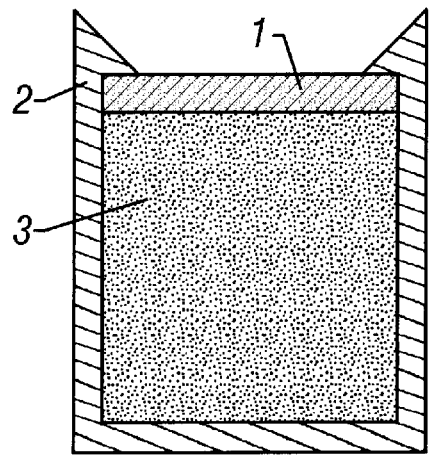
FIG. 2 is a schematic showing an exposed side view of an embodiment of the device. In this embodiment, the member for inhibiting flow from the absorbent material to the filter is not present.

In a preferred embodiment, a member 4 for inhibiting flow from the absorbent material to the filter may be placed in between the filter 1 and the absorbent material 3. This member 4 for inhibiting flow may serve to reduce backflow in the filter device. In a preferred embodiment, the member 4 for reducing backflow may be a porous polyethylene disk placed in between the filter 1 and the absorbent material 3. The disk may enhance the drawing of the fluid into the absorbent material 3 and minimizes backflow toward the filter 1. In a particularly preferred embodiment, the porous polyethylene disk may be a POREX® polyethylene disk, or its equivalent. However, as depicted in FIG. 2, the device may also function without the member 4 for reducing backflow.

Persons of ordinary skill in the art will readily realize that other embodiments of the device are possible. For example, the device may utilize a variety of other filters for retaining the crystals. The filter may be placed into a bowl-shaped or conical-shaped device and the urine or biological fluid drawn through by suction, gravity, external pressure or other means. This would enable almost any filter to be used in the device which had pores small enough to retain the crystals suspected of being present and was, preferably, capable of resisting staining or of being destained. Typically, this would enable any filters with pores of at least approximately 0.2 $\mu$m or larger to be used. The selection of an optimal filter can result in greater ease of reading the assay results. The filter should be selected based on the type of crystals being detected since each crystal has its own typical range of size where it becomes clinically important. Optimal results are obtained by selecting a filter which has pore sizes which are the largest that will still capture the crystal of interest. Smaller pore sizes than necessary may reduce flow efficiency and also capture interfering substances, such as cellular debris, casts, bacteria, sperm, or other biological products which may interfere with the indicator reaction since they may contain magnesium, calcium, or other components which may be detected by the indicator.

Figure 3:
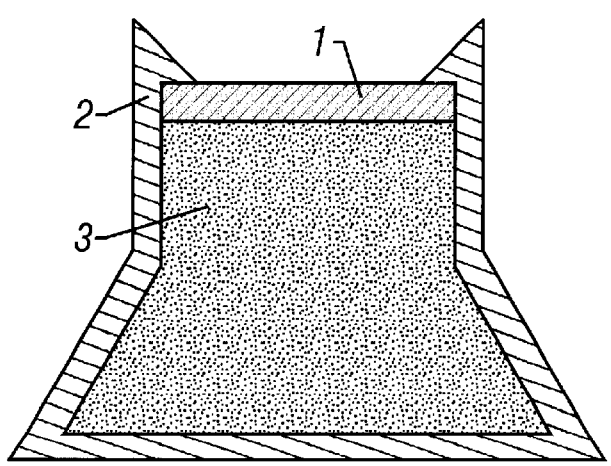
FIG. 3 is a schematic illustrating that the device may take a variety of shapes. The Figure is an exposed side view and the shape here depicted may be useful for absorbing larger quantities of liquids where desirable.
Figure 4:
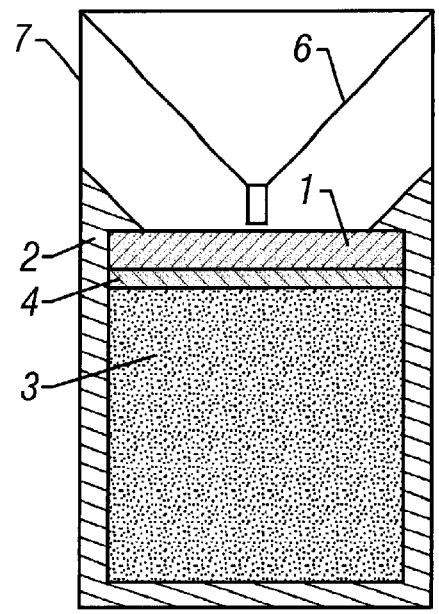
FIG. 4 is a schematic illustrating an exposed side view of an embodiment of the device where a funnel may be attached to the device for receiving the sample of biological fluid.

In other embodiments, the housing 2 may have a lower opening into which is inserted a removable plug to permit insertion of the filter 1, the member 4 for inhibiting flow from the absorbent material to the filter, and the absorbent material 3. The size of the absorbent material 3 is preferably selected such that all of the liquid to be added to the apparatus during an assay can be received in and retained in the absorbent material 3. Small ports for venting air, may be provided in the housing 2 near the bottom to allow displaced air to escape. Other embodiments may include, but are not limited to, shapes which facilitate the use of the device under vacuum or positive pressure. FIG. 3 depicts an embodiment of the device shaped to maximize the absorptive capability of the device. FIG. 4 depicts an embodiment of the device with a funnel 6 for directing sample to the filter 1, so as to concentrate crystals at one spot for better detection. The funnel may have a side 7 which is secured to the device by any suitable fastening method such as clipping or gluing. In preferred embodiments, the funnel may be made of plastic.

The person of ordinary skill will also understand that the invention can operate according to other principles. For example, a filter 1 may be used which has the qualities of retaining crystals by electrostatic attractions, or by chemical affinity, or any method which serves to secure the crystals which may be present to the surface of the filter 1 or within its structure, for staining and detection.

The present invention is also directed to methods of detecting and identifying crystals which may be present in urine or other biological fluid. In one embodiment, a method is provided which consists of the steps of applying the sample to the receiving area of the device 5 of the present invention (referring to FIG. 1 throughout); a first wash step which may be desirable in some chemistries (such as when assaying for struvite or oxalate crystals) to wash away contaminants or non-crystal material which may be present from the biological fluid, and which may also expose a determining component of the crystals; a step whereby an indicator reagent or system is applied to the crystals which may be present on the surface of or within the structure of the filter 1; in some chemistries, such as when using dye binding as a means of visualization, as in a preferred test for struvite crystals, an additional wash step such as to destain the filter 1 which may be desirable for optimal visualization of crystal coloration which may have occurred; and, a step in which coloration and identity of the crystals which may be present is determined.

In a preferred embodiment, the sample is applied directly to the filter 1 of the device. This may be accomplished by dropwise addition or simply by pouring or pipetting the sample into the receiving vessel or area of the device 5. In a preferred embodiment the biological fluid is drawn through the filter 1 and into the absorbent material 3 and the crystals are retained on the surface of the filter 1 or within its structure. In a more preferred embodiment, the biological fluid is drawn through the filter 1 and through the member 4 for inhibiting flow from the absorbent material to the filter (if present), and into the absorbent material 3. The member 4 for inhibiting flow may serve to reduce backflow in the device. In other embodiments, the fluid may be passed through the filter 1 by the use of suction, gravity, external pressure, or any other means which will cause the fluid to pass through the filter 1. In preferred embodiments, the filter 1 is assembled with the absorbent material 3 in a manner which permits direct communication between the pores or interstices of the filter 1 and the capillaries of the absorbent material 3. Thus, as a liquid is applied to the filter 1 and saturates it, the liquid is drawn into the absorbent material 3. As a result, flow can be induced through the filter 1 when a liquid sample is applied to it even though the hydrostatic pressure of the fluid is so low that unaided it could not flow through the filter 1 without the application of pressure to force it through or a vacuum to draw it through.

The crystals which may be present are thereby separated from the biological fluid and retained on the surface of the filter 1, or within its structure. A wash step may then be carried out to remove soluble material and any material other than the crystals from the surface. This step is desirable when the sample contains soluble cross reactive or interfering substances. The wash step may also accomplish a disintegration action upon the crystals and help to expose a determining component of the crystals such as $Ca^{+2}$ or oxalate. By partially disintegrating the crystals the available concentration of analyte is dramatically increased. A disintegration action is an action which at least partially disintegrates the crystal. The disintegration action releases free analyte into a larger area and facilitates visualization of crystals which may be present. A determining component is a property of the crystal which is particular for a specific crystal type or a group of crystal types such that identification of the presence of the determining component aids in some way in identifying the crystal type. An indicator system is a reagent or group of reagents which produce a detectable signal in the presence of a determining component. An indicator reagent is a chemical entity which is able to produce a detectable signal in the presence of a determining component.

An indicator reagent such as a dye or enzymatic substrate which is specific for a determining component of the type of crystal being tested for may then be contacted with the crystals. Suitable indicator reagents may include, but are not limited to, the combination of oxalate oxidase, horseradish peroxidase, and an indicator dye, magnesium binding dyes (such as magneson dye) which bind to magnesium, precipitating dyes, or calcium binding dyes which bind to calcium. Those of ordinary skill in the art will realize that the dyes can be added in combination with the other reagents or can be added afterwards. The person of ordinary skill will also realize that a wide variety of other indicator reagents are available and may be utilized, as long as the presence of some determining component of the crystals which may be present is detected by the indicator reagent. Therefore, the above indicators are provided as examples, and are not intended to be limiting.

In some chemistries, depending on the presence or absence of substances such as residual dyes that obscure visual results, a final wash step may be desirable to provide optimal viewing of any color change or other indicating signal which may be present. The presence of crystals and their composition can then be determined by noting coloration of the filter 1 or other indicating signals which may have occurred due to the action of a specific dye, enzyme, or other indicator reagent on the crystals or crystal components.

The methods of the present invention fill the need for a method to quickly detect the presence of crystalluria, and for determining the type of crystal which may be present in a novel, heretofore undisclosed way.

The methods and principles disclosed herein may be adapted and applied for use in detecting crystals from any biological fluid. For example, many valuable products may be produced in crystalline form from cell culture or fermentation processes. These products may include biological components, antibiotics, or any product produced in crystalline form. Crystalluria also occurs in humans and may be the result of the presence of various drugs which are excreted in the urine, such as ampicillin, primidone, and ciprofloxicin. The devices and methods of the present invention can be adapted and applied to detect these crystals as well. These methods and principles may also be applied to detect crystals which may be present in whole blood, blood products such as plasma or serum, or interstitial fluid.

The present invention also provides kits with materials and reagents necessary for conducting the method. The kits may contain devices and reagents useful for detecting and identifying crystals which may be present in urine or other biological fluids. In a particularly preferred embodiment, the kit may contain: a) a device for detecting crystals which may be present in a biological fluid, b) a container of 0.1N HCl, c) a container of 0.5% magneson dye in 1% NaOH and d) a container of 0.1N NaOH. In another particularly preferred embodiment, the kit may contain a) a device, b) a container of 10 mmol/L EDTA wash buffer at approximately pH 7.6, c) a container of 3-methyl-2-benzothiazolinone hydrazone (MBTH), d) a container of 3-(dimethylamino) benzoic acid (DMAB) in a buffer, e) a container of oxalate oxidase, and f) a container of horseradish peroxidase. The person of ordinary skill will easily imagine that in various embodiments these components may be contained in various combinations. Various embodiments of the kits may include kits containing only a device, or all or some of the reagents useful for conducting a single assay or a group of assays.

The following examples illustrate the operation of particular embodiments of the invention and should not be construed as limiting. The person of ordinary skill will recognize that the assays and concepts illustrated may be applied and modified to enable the detection of many types of crystals.

EXAMPLE 1

This example illustrates how the present invention can be employed to detect the presence of struvite (magnesium-ammonium-phosphate) crystals in urine.

Fourteen urine samples from dogs and cats were analyzed. A HEMASEP V® filter was placed over two blocks of cellulose absorbent material and secured within an ICON® filter holder. Reagent 1 consisted of 0.1N HCl, Reagent 2 was 0.5% magneson dye in 1% NaOH, and Reagent 3 was 0.1N NaOH.

Ten drops of sample urine were applied to the filter and allowed to absorb. One drop of 0.1N HCl was used to wash debris and contaminants into the absorbent material, while simultaneously causing the partial disintegration of the crystal. When the HCl was completely absorbed, one drop of the 0.5% magneson dye in 1% NaOH (Reagent 2) was added. After absorption of Reagent 2, the filter had a purple color. A final wash with approximately 1 ml of 0.1N NaOH (Reagent 3) revealed that the filter material was white for some samples, indicating that no magnesium and hence no struvite crystals were present in those samples. In other samples, a blue precipitate had formed, indicating the presence of magnesium and that struvite crystals were present.

EXAMPLE 2

This example illustrates how the invention may be employed to test for the presence of oxalate crystals, which may occur as calcium, ammonium or magnesium oxalates. Calcium oxalates are the most commonly found oxalate crystal in veterinary medicine.

In this embodiment, Reagent 1 was a 10 mM EDTA wash buffer at pH 7.6, Reagent 2 was prepared immediately before use from its separate compositions, and contained 3-methyl-2-benzothiazolinone hydrazone (MBTH) and 3-(dimethylamino) benzoic acid (DMAB) in succinate buffer, combined with oxalate oxidase and horseradish peroxidase. Oxalate oxidase acts upon calcium oxalate crystals in the presence of oxygen to convert oxalate to carbon dioxide and hydrogen peroxide. A detectable indamine dye is produced by the interaction of the DMAB/MBTH substrate with hydrogen peroxide in the presence of peroxidase.

A drop of sample urine was applied to a HEMASEP L® filter and allowed to absorb. Approximately 1 ml of Reagent 1 was added, which binds interfering agents and washes contaminants into the absorbent material while also preparing the crystals for enzymatic activity by Reagent 2. After the absorption of Reagent 1 was complete, 110 µl of Reagent 2 was added. The development of a blue-purple color within approximately ten minutes indicated the presence of oxalate crystals.

While the present examples describe the preferred methods and techniques of practicing the invention, the invention is broadly applicable for detecting and identifying a variety of crystal types using various indicator reagents. For example, crystals containing calcium may also be detected by using cresolpthalein complexone or arsenazo III. With these indicators, a disintegration step may be necessary to break up the crystals. Similarly, calgamite may be used to detect and stain crystals containing magnesium. And crystals containing uric acid may be detectable in the blood, urine, or other biological fluid with the enzyme uricase. These examples are intended only as some embodiments which are possible and are not meant to exclude indicator means or crystals which may be later discovered.

The above examples relating to the present invention, should not, of course, be construed as limiting the scope of the invention. Such variations of the invention, now known or later developed, which would fall within the purview of those of ordinary skill in the art are to be considered as falling within the scope of the invention as hereinafter claimed.

It should be understood that although the present invention has been specifically disclosed by preferred embodiments and optional features, modification and variation of the concepts herein disclosed may be resorted to by those of ordinary skill in the art, and that such modifications and variations are considered to be within the scope of this invention as defined by the appended claims.

What is claimed is:

1. A method of detecting and identifying crystals suspected of being present in a biological fluid, comprising:
    a) isolating the crystals on or within a filter;
    b) contacting the crystals with an indicator reagent specific for a determining component of the crystals; and
    c) determining the presence and identity of the crystals.

2. The method of claim 1 further comprising a step of washing the crystals.

3. The method of claim 2 wherein the step of washing the crystals also accomplishes a disintegration action upon the crystals.

4. The method of claim 1 further comprising the step of washing the crystals after contact with the indicator reagent.

5. The method of claim 1 wherein the biological fluid is urine, blood, a blood product, or interstitial fluid.

6. The method of claim 1 wherein the biological fluid is urine.

7. The method of claim 1 wherein the crystals suspected of being present are oxalate crystals.

8. The method of claim 7 wherein the indicator system is oxalate oxidase and horseradish peroxidase and an indicator dye.

9. The method of claim 1, wherein the crystals suspected of being present are struvite crystals.

10. The method of claim 9 wherein the indicator reagent comprises a magnesium binding dye.

11. The method of claim 10 wherein the magnesium binding dye is magneson dye.

12. The method of claim 1 wherein the indicator reagent comprises a calcium binding dye.

13. A method of detecting and identifying crystals suspected of being present in a biological fluid, comprising:
    a) isolating the crystals on or within a filter,
    b) at least partially disintegrating the crystals;
    c) contacting the crystals with at least one indicator reagent specific for a determining component of the crystals; and
    d) determining the presence and identity of the crystals.

14. The method of claim 13 further comprising the step of destaining the filter to improve visualization of the result.

15. The method of claim 13 wherein the step of at least partially disintegrating the crystals comprises washing the crystals.

16. The method of claim 13 wherein the biological fluid is urine, blood, a blood product, or interstitial fluid.

17. The method of claim 16 wherein the biological fluid is urine.

18. The method of claim 13 wherein the crystals suspected of being present are oxalate crystals.

19. The method of claim 18 wherein the indicator reagents comprise oxalate oxidase, a peroxidase, and an indicatory dye.

20. The method of claim 13 wherein the crystals suspected of being present are struvite crystals.

21. The method of claim 20 wherein the indicator reagent (s) comprise a magnesium binding dye.

22. The method of claim 21 wherein the magnesium binding dye is magneson dye.

23. The method of claim 13 wherein the indicator reagent (s) comprises a calcium binding dye.

* * * * *